United States Patent
Jeong

(10) Patent No.: US 12,087,445 B2
(45) Date of Patent: Sep. 10, 2024

(54) AUTOMATIC CERVICAL CANCER DIAGNOSIS SYSTEM

(71) Applicant: AIDOT INC., Seoul (KR)

(72) Inventor: Jae Hoon Jeong, Seongnam-si (KR)

(73) Assignee: AIDOT INC., Seoul (KR)

( * ) Notice: Subject to any disclaimer, the term of this patent is extended or adjusted under 35 U.S.C. 154(b) by 382 days.

(21) Appl. No.: 17/616,336

(22) PCT Filed: Dec. 13, 2019

(86) PCT No.: PCT/KR2019/017679
§ 371 (c)(1),
(2) Date: Dec. 3, 2021

(87) PCT Pub. No.: WO2020/246676
PCT Pub. Date: Dec. 10, 2020

(65) Prior Publication Data
US 2022/0328186 A1    Oct. 13, 2022

(30) Foreign Application Priority Data

Jun. 4, 2019  (KR) .................. 10-2019-0066163
Sep. 4, 2019  (KR) .................. 10-2019-0109333

(51) Int. Cl.
*G16H 50/20*     (2018.01)
*A61B 5/00*      (2006.01)
(Continued)

(52) U.S. Cl.
CPC ............. *G16H 50/20* (2018.01); *A61B 5/004* (2013.01); *A61B 5/1032* (2013.01);
(Continued)

(58) Field of Classification Search
CPC ........ G16H 50/20; G16H 30/40; G16H 50/70; A61B 5/004; A61B 5/1032; A61B 5/4331;
(Continued)

(56) References Cited

U.S. PATENT DOCUMENTS 6,135,965 A * 10/2000 Tumer ................. A61B 5/0071
                                                         600/408
9,934,364 B1 * 4/2018 Kumar ................... G06N 3/045
(Continued)

FOREIGN PATENT DOCUMENTS

CN    107220975 A    9/2017
CN    108288506 A    7/2018
(Continued)

OTHER PUBLICATIONS

Das, Abhishek, Preprocessing for Automating Early Detection of Cervical Cancer, 2011, IEEE, 15th International Conference on Information Visualisation, 2011, pp. 597-600 (Year: 2011).*
(Continued)

*Primary Examiner* — Lewis G West
(74) *Attorney, Agent, or Firm* — Stein IP, LLC

(57) ABSTRACT

The present invention relates to an automatic cervical cancer diagnosis system for performing machine learning by classifying cervical data required for automatic diagnosis of cervical cancer according to accurate criteria and automatically diagnosing cervical cancer based on the machine learning, the automatic cervical cancer diagnosis system including: a learning data generator configured to classify unclassified photographed image data for a cervix transmitted from an external device or a storage according a combination of multi-level classification criteria to generate learning data for each new classification criterion in a learning mode; a photographed image pre-processer config-
(Continued)

ured to pre-process photographed cervix images; a cervical cancer diagnoser including a machine learning model for cervical cancer that learns a characteristic of the learning data generated for each classification criterion in the learning mode, wherein the machine learning model generates diagnosis information about whether cervical cancer has occurred with respect to the pre-processed photographed cervix image; a screen display controller configured to display and output a user interface screen configured to display the diagnosis information and inputting evaluation information according to a reading specialist; a retraining data generator configured to extract information required for retraining from the evaluation information input through the user interface screen and request retraining the machine learning model; and a diagnosis and evaluation information storage configured to store the diagnosis information about whether cervical cancer has occurred and the evaluation information input through the user interface screen.

10 Claims, 11 Drawing Sheets

(51) Int. Cl.
 *A61B 5/103* (2006.01)
 *G06N 20/00* (2019.01)
 *G16H 30/40* (2018.01)
 *G16H 50/70* (2018.01)
(52) U.S. Cl.
 CPC .......... *A61B 5/4331* (2013.01); *A61B 5/7267* (2013.01); *G06N 20/00* (2019.01); *G16H 30/40* (2018.01); *G16H 50/70* (2018.01)
(58) Field of Classification Search
 CPC .... A61B 5/7267; G06N 20/00; G06N 3/0464; G06N 20/20
 See application file for complete search history.

(56) References Cited

U.S. PATENT DOCUMENTS

| | | | | |
|---|---|---|---|---|
| 10,127,665 | B1 | 11/2018 | Ding et al. | G06T 7/0014 |
| 10,360,499 | B2* | 7/2019 | Kumar | G16B 40/20 |
| 10,599,984 | B1* | 3/2020 | Wubbels | G16H 50/20 |
| 11,080,855 | B1* | 8/2021 | Beck | G16H 50/30 |
| 2010/0092064 | A1* | 4/2010 | Li | A61B 5/7264 382/133 |
| 2012/0283574 | A1* | 11/2012 | Park | G06F 18/253 600/476 |
| 2013/0089248 | A1* | 4/2013 | Remiszewski | G06V 20/698 382/128 |
| 2019/0252073 | A1* | 8/2019 | Hsu | G06T 7/0012 |
| 2019/0304092 | A1* | 10/2019 | Akselrod-Ballin | G06N 3/084 |
| 2022/0377227 | A1* | 11/2022 | Jeong | A61B 1/0005 |

FOREIGN PATENT DOCUMENTS

| | | |
|---|---|---|
| CN | 108647731 A | 10/2018 |
| JP | 2010-204966 A | 9/2010 |
| JP | 2013-526930 A | 6/2013 |
| JP | 2017-224327 A | 12/2017 |
| KR | 10-0850347 B1 | 7/2008 |
| KR | 10-2013-0012297 A | 2/2013 |
| KR | 10-2014-0104946 A | 8/2014 |
| KR | 10-2015-0015976 A | 2/2015 |
| KR | 10-2016-0047720 A | 5/2016 |
| KR | 10-2018-0135898 A | 12/2018 |
| KR | 10-2041402 B1 | 10/2019 |
| KR | 10-2020-0126303 A | 11/2020 |
| WO | WO 2019/098415 A1 | 5/2019 |
| WO | WO 2018/221689 A | 4/2020 |

OTHER PUBLICATIONS

Korean Office Action dated Mar. 29, 2021, issued to the corresponding Korean Application No. 10-2019-0109333.
Korean Notice of Allowance dated Oct. 12, 2021, issued to the corresponding Korean Application No. 10-2019-0109333.
International Search Report dated Apr. 8, 2020, issued to the corresponding International Application No. PCT/KR2019/017679.
First Office Action mailed Aug. 25, 2023, issued to corresponding Chinese Application No. 201980036662.5.
Notice of Allowance mailed Aug. 8, 2023, issued to corresponding Japanese Application No. 2021-572002.
Office Action mailed Mar. 29, 2021, issued to corresponding Japanese Application No. 2021-572002.

* cited by examiner

[CERVICAL CYTOLOGY EXAMINATION]

[IMAGE OF CERVICOGRAPHY EXAMINATION]   [METHOD OF BIOPSY]

[CERVICOGRAPHY SCREENING]

AUTOMATIC CERVICAL CANCER DIAGNOSIS SYSTEM

CROSS-REFERENCE TO RELATED APPLICATIONS

This application is a national stage of International Application No. PCT/KR2019/017679, filed Dec. 13, 2019, which claims the benefit of Korean Application No. 10-2019-0066163, filed Jun. 4, 2019, and Korean Application No. 10-2019-0109333, filed Sep. 4, 2019, in the Korean Intellectual Property Office, the disclosure of which is incorporated herein by reference.

TECHNICAL FIELD

This invention relates to an automatic cervical cancer diagnosis system, and specifically, an automatic cervical cancer diagnosis system for performing machine learning by classifying cervical data required for automatic diagnosis of cervical cancer according to accurate criteria and automatically diagnosing cervical cancer based on the machine learning.

BACKGROUND ART

Cervical cancer is ranked in the top range of cancers that women fear because the involved hysterectomy may affect pregnancy and childbirth, and there is a concern of losing one's identity as a woman.

According to statistics in 2013, the number of cervical cancer patients in Korea is 26,207, and cervical cancer is ranked 4th among female cancers (data from the Ministry of Health and Welfare). In addition, cervical cancer is one of the seven major cancers recommended for screening in Korea, and as cervical cancer is included in the national cancer screening project in 1999, the rate of early diagnosis is increasing. In recent years, cervical epithelial cancer (a precancerous stage), referred to as a '0' stage cervical cancer, is also on the rise, and women with sexual experience are advised to have an annual checkup.

As for the current status of the screening market, first, the rate of cervical epithelial cancer in young women is increasing, and since 2016, the age of screening subjects has been lowered from 30 to 20. In particular, unlike other cancers, health insurance benefits cover 300% of the screening costs related to cervical cytology. However, since the false negative rate (i.e., the misdiagnosis rate) of screenings reaches a maximum of 55%, it is recommended to perform a cervicography together with cervical cytology as a complementary test. As of 2013, the global cervical cancer screening market was about 6.86 trillion Won, in which cervicography has a 30% market share, amounting to about 2 trillion Won.

FIG. 1 shows conceptual diagrams schematically illustrating a method of cervical cytology and cervicography to diagnose cervical cancer according to the conventional process. Referring to the lower part of FIG. 1, when a photographed image of the cervix is acquired from the outside of the vagina of a female subject through a predetermined photographing device (for example, a colposcope shown in FIG. 1), the photographed image is analyzed and the result is used so that the misdiagnosis rate for cervical cancer is reduced.

However, when using the conventional colposcope, the medical staff checks whether cervical cancer has occurred with respect to the cervix image in the light of education and experience thereof, but such a method is iterative and confusing in many cases so that even an experienced doctor takes a long time and the accuracy is also low.

In order to overcome such a shortcoming, there has been introduction of apparatuses for determining the onset of cervical cancer capable of acquiring photographed images of the cervix and generating and providing information about whether cervical cancer of a subject has occurred based on a machine learning model for cervical cancer from the acquired cervical images.

Main factors for evaluating the performance of the determination apparatuses is that images to be used for learning need to be accurately classified and organized to proceed with learning. Without such data being accurately and clearly classified, the accuracy of analysis on the onset of cervical cancer may inevitably decrease. In general, unlike general medical images, cervical cancer colposcopy images are represented in various different forms depending on the photography environment and the photographer. Therefore, apparatuses for determining the onset of cervical cancer are required to classify images to be used for learning according to more clear and strict criteria to proceed with learning.

In addition, even when machine learning is performed by classifying learning data according to clear and strict criteria, misdiagnosis may occur in the result of diagnosis (analysis), and thus there is an urgent need for introduction of a system for allowing the results to be evaluated by specialists to increase the reliability of the analysis apparatuses for automatically diagnosing cervical cancer based on machine learning or for aiding in diagnosis performance of the analysis apparatuses.

RELATED ART DOCUMENT

Patent Document (PATENT DOCUMENT 0001) Korean Registered Patent No. 10-0850347
(PATENT DOCUMENT 0002) Korean Laid-open Patent Publication No. 10-2016-0047720

SUMMARY OF INVENTION

Technical Problem

Accordingly, the present invention is an invention devised according to the above-described need, and the main object of the present invention is to provide an automatic cervical cancer diagnosis system for performing machine learning by classifying cervical cancer learning data required for automatic diagnosis of cervical cancer according to accurate criteria and automatically diagnosing cervical cancer based on the machine learning.

Further, another object of the present invention is to provide an automatic cervical cancer diagnosis system capable of preventing learning from being excessively performed on one specific form of cervical images or preventing no learning from being performed on another specific form of cervical images so that accurate cervical diagnosis is allowed to be performed.

In addition, another object of the present invention is to provide an automatic cervical cancer diagnosis system capable of providing a reading specialist (a specialist) with various pieces of information automatically analyzed based on a machine learning model so that that convenience of reading is ensured while configuring a user interface screen such that input information evaluated by a reading specialist is used for real time retraining so that the performance of the machine learning model is continuously improved.

Solution to Problem

An automatic cervical cancer diagnosis system according to an embodiment of the present invention to achieve the above described objects is characterized in including:
- a learning data generator configured to classify unclassified photographed image data for a cervix transmitted from an external device or a storage according to a combination of multi-level classification criteria to generate learning data for each new classification criterion in a learning mode;
- a photographed image pre-processer configured to pre-process photographed cervix images;
- a cervical cancer diagnoser including a machine learning model for cervical cancer that learns a characteristic of the learning data generated for each classification criterion in the learning mode, wherein the machine learning model generates diagnosis information about whether cervical cancer has occurred with respect to the pre-processed photographed cervix image;
- a screen display controller configured to display and output a user interface screen configured to display the diagnosis information and inputting evaluation information according to a reading specialist;
- a retraining data generator configured to extract information required for retraining from the evaluation information input through the user interface screen and request retraining the machine learning model; and
- a diagnosis and evaluation information storage configured to store the diagnosis information about whether cervical cancer has occurred and the evaluation information input through the user interface screen.

In the configuration of the above described system, the learning data generator may be characterized in applying mirroring or cropping to the learning data for each classification criterion to generate additional learning data such that a numerical balance of the learning data for each classification criterion is adjusted.

Further, the learning data generator may be characterized in
classifying the unclassified photographed image data using a combination of at least two classification criteria among a first level classification criterion having a color as a classification criterion, a second level classification criterion having a size of the cervix in photographed image data as a classification criterion, a third level classification criterion having a combination of a color and a form in cervical image data as a classification criterion, and a fourth level classification criterion having an exposure and a focus as a classification criterion.

In some cases, the learning data generator may be characterized in
firstly classifying the unclassified photographed image data for the cervix according to a first level classification criterion having a color as a classification criterion, secondarily classifying the unclassified photographed image data for the cervix according to a second level classification criterion having a size of the cervix in the firstly-classified unclassified photographed image data as a classification criterion, and thirdly classifying the unclassified photographed image data according to a third level classification criterion having a combination of a color and a form in the secondarily-classified unclassified photographed image data as a classification criterion.

Meanwhile, in the automatic cervical cancer diagnosis system, the first level classification criterion may include color values for identifying each of an acetic acid reaction image, a Lugol's solution reaction image, a green filter image, and a general image as a classification criterion value, and
the third level classification criterion may include a combination of a color value and a shape for identifying one or more among blood, mucus, a loop, a colposcope, a treatment trace, and a surgical instrument in the cervical image data as a classification criterion value.

Further, the cervical cancer diagnoser may be characterized in generating the diagnosis information including classification information regarding being negative, atypical, benign, and malignant for cervical cancer with respect to a photographed cervix image of a subject, accuracy information of the classification information, negative/positive determination information, and morphological opinion information based on the machine learning model.

The screen display controller may be characterized in displaying and outputting a screen that is divided into an entire or partial display area of a photographed cervix image of a subject, a history information display area of another image of the subject photographed at a previous time, a subject information exposure area, a negative/positive determination information input area, a morphological opinion information input area, a technical defect information input area regarding a quality of a photographed image, an output area of the diagnosis information derived based on the machine learning model, and a reading specialist opinion input area as the user interface screen.

Advantageous Effects of Invention

As is apparent from the above, the automatic cervical cancer diagnosis system according to the embodiment of the present invention trains an artificial intelligence network, such as a machine learning model, by classifying unclassified photographed image data for a cervix according to a combination of multi-level classification criteria so that learning is achieved on image data having more diverse characteristics compared to when training the artificial intelligence network based on data classified using a classification criterion having only one characteristic (a color, a shape, brightness, etc.) so that lesions can be more accurately diagnosed.

In addition, the present invention further generates additional learning data to adjust the numerical balance of learning data for each classification criterion and allows the additional learning data to be used for learning so that learning is prevented from being excessively performed only for one specific form of cervical (cancer) image data, or no learning is prevented from being performed on another specific form of cervical image data so that the presence or absence of lesions on the cervix can be accurately diagnosed.

Further, the present invention automatically diagnoses the presence or absence of a lesion related to cervical cancer based on a machine learning model and displays the result externally through a user interface screen such that a reading specialist is guided to input evaluation information on the user interface screen and some of the evaluation information is extracted to be used for retraining the machine learning model so that the performance of the machine learning model can be continuously upgraded.

DETAILED DESCRIPTION OF EMBODIMENT

Figure 1:
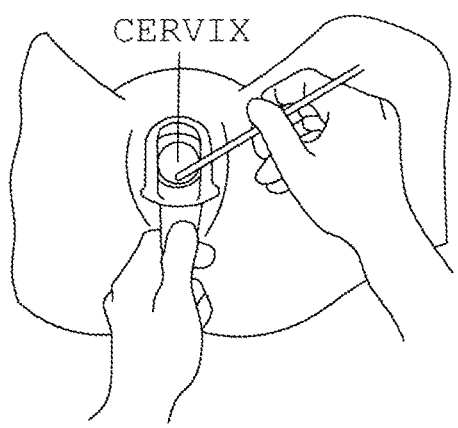
FIG. 1 shows schematic conceptual diagrams illustrating a method of performing cervical cytology and cervicography to diagnose cervical cancer according to the conventional process.
Figure 1:
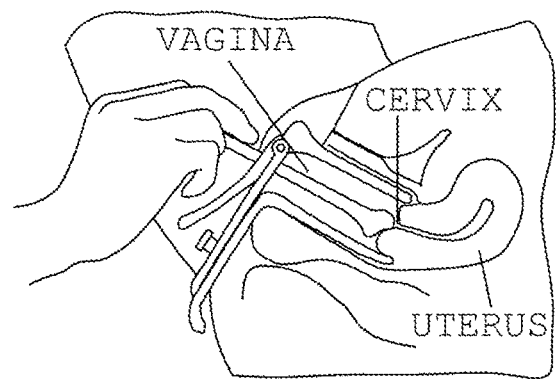
Figure 1:
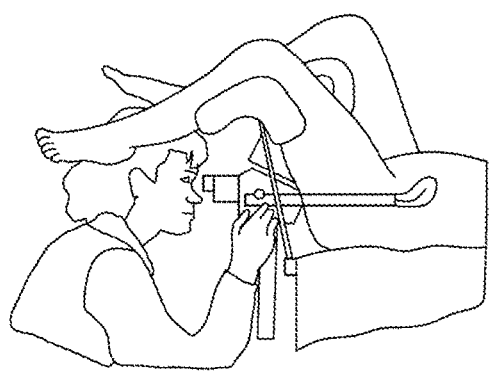
Figure 1:
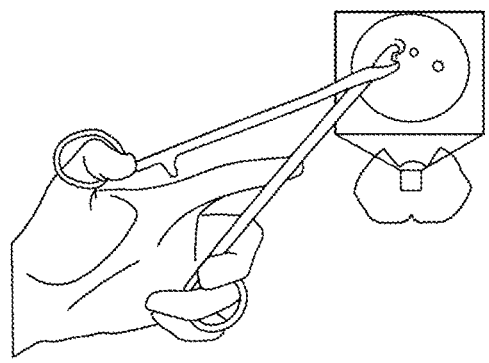

In the following detailed description, reference is made to the accompanying drawings that show, by way of illustration, specific embodiments in which the invention may be practiced such that objectives, technical solutions, and advantages become readily apparent. These embodiments are described in sufficient detail to enable those skilled in the art to practice the invention.

In the detailed description and claims of the present invention, "learning" is a term referring to performing machine learning according to a procedure, and it will be understood that the term is not intended to refer to a mental action, such as human educational activity. In addition, in the detailed description and claims of the present invention, it will be understood the term "including" and modifications thereof is not intended to preclude other technical features, additions, components, or steps. Other objects, advantages, and features of the present invention will become apparent to those skilled in the art, in part from this description, and in part from the practice of the present invention. The examples and drawings below are provided by way of example and are not intended to limit the present invention. In addition, the present invention covers all possible combinations of the embodiments indicated herein. It will be understood that the various embodiments of the invention, although different, are not necessarily mutually exclusive. For example, a certain feature, structure, or characteristic described herein in connection with one embodiment may be implemented within other embodiments without departing from the spirit and scope of the invention. In addition, it will be understood that the location or arrangement of individual elements within each disclosed embodiment may be modified without departing from the spirit and scope of the invention. The following detailed description is, therefore, not to be taken in a limiting sense, and the scope of the present invention is defined only by the appended claims, appropriately interpreted, along with the full range of equivalents to which the claims are entitled. In the drawings, like numerals refer to the same or similar functionality throughout the several views. As used herein, the singular forms "a," "an," and "the" are intended to include the plural forms as well, unless the context clearly indicates otherwise. In the description of the embodiments, a detailed description of related known functions or constructions will be omitted to avoid obscuring the subject matter of the present invention.

Hereinafter, exemplary embodiments of the present invention will be described in detail with reference to the accompanying drawings in order to enable those skilled in the art to easily practice the present invention.

For reference, a convolutional neural network (CNN) model, which is one of machine learning models used in the present invention, may be briefly defined as a form of artificial neural networks stacked in multiple layers. In other words, the CNN model is expressed as a deep neural network in the meaning of a deep-structured network and is provided in a form of a multi-layered network structure in which a large amount of data is learned so that features of images are automatically learned, and the learning of the network proceeds in a way which minimizes the error of an objective function. Since the configuration is also represented as a connection between neurons in the human brain, the CNN has become a representative of artificial intelligence. In particular, the CNN is a model suitable for classifying two-dimensional images, such as still images, and repeats a convolution layer that generates a feature map using a plurality of filters for each region of the image and a pooling layer (a sub-sampling layer) that reduces the size of the feature map and extracts features that are invariant with change in position or rotation so that various levels of features may be extracted from points, lines, and surfaces of low-level features to complex and meaningful features of high-level features, and finally, by using features extracted through a fully-connected layer as input values of the existing model, a classification model with higher accuracy may be constructed.

Figure 2:
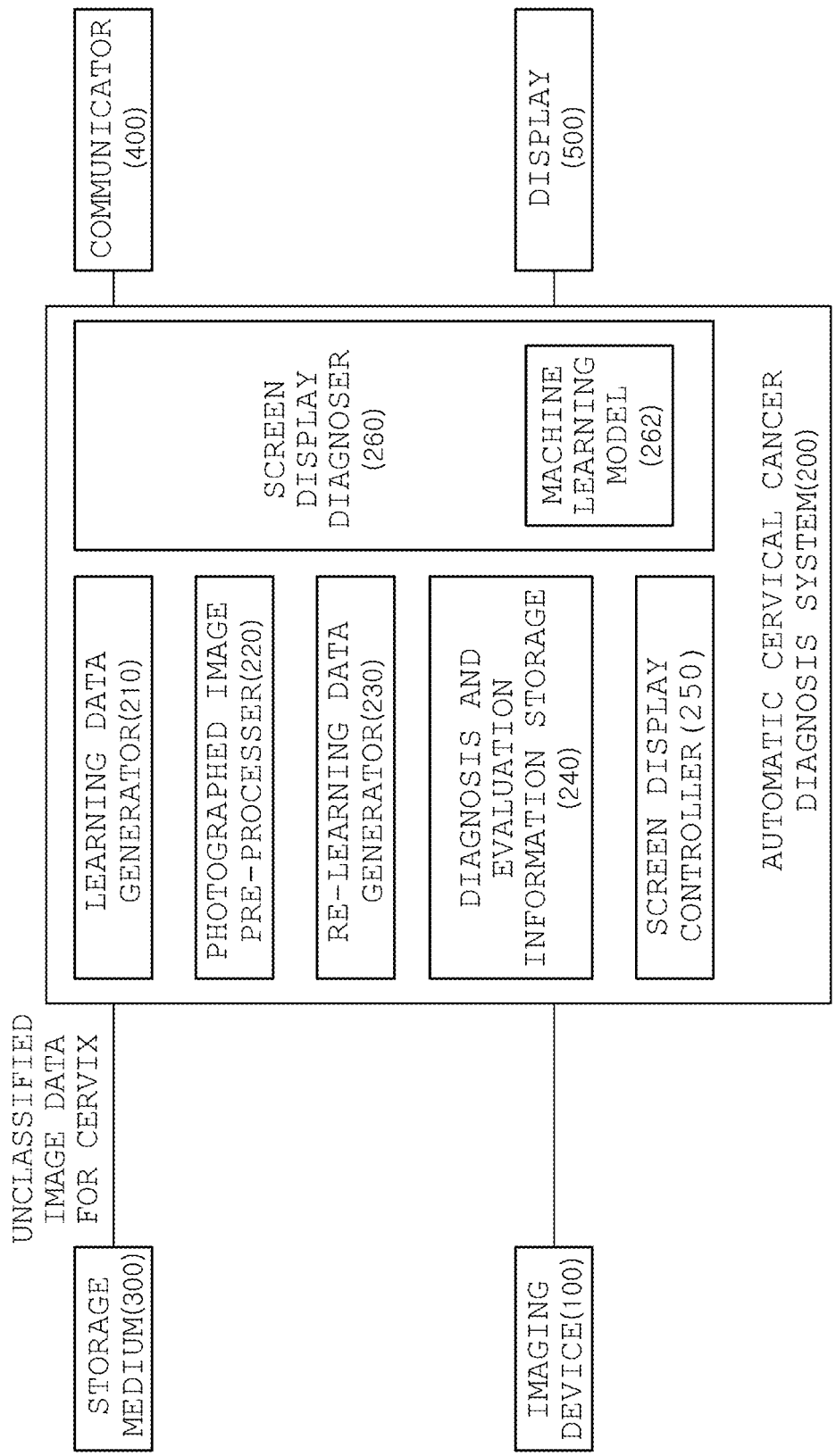
FIG. 2 is an exemplary view illustrating a configuration of an automatic cervical cancer diagnosis system according to an embodiment of the present invention.

FIG. 2 is a block diagram illustrating an automatic cervical cancer diagnosis system according to an embodiment of the present invention. Referring to FIG. 2, an automatic cervical cancer diagnosis system 200 according to the embodiment of the present invention may be a computer system or a server computer system that operates in combination with an imaging device 100, a storage medium 300, a communicator 400, and a display 500 and may be implemented as a collection of executable code data (a form of an application program) installed in a memory of the computer system.

Referring to FIG. 2, the automatic cervical cancer diagnosis system 200 according to the embodiment of the present invention may directly or indirectly communicate with a computing device (not shown) of a reading specialist located at a remote site through the communicator 400. The reading specialist may directly (using a keyboard or mouse) input evaluation information to be described below through a user interface screen displayed on the display 500.

The imaging device 100, in a diagnosis mode, acquires a photographed cervix image of a subject and transmits the photographed cervix image to the automatic cervical cancer diagnosis system 200 to be described below, and the storage medium 300 stores unclassified photographed image data for the cervix, which will be described below, that is to be learned by the machine learning model.

Hereinafter, a detailed configuration of the automatic cervical cancer diagnosis system 200 will be described with reference to FIG. 2, and the automatic cervical cancer diagnosis system 200 according to the embodiment of the present invention includes

- a learning data generator 210 configured to classify unclassified photographed image data for a cervix transmitted from an external device or a storage (the storage medium 300) according to a combination of multi-level classification criteria to generate learning data for each new classification criterion in a learning mode,
- a photographed image pre-processer 220 configured to perform pre-processing (image quality improvement, blurring, noise processing) on photographed cervix images,
- a cervical cancer diagnoser 260 including a machine learning model for cervical cancer that learns a characteristic of the learning data generated for each classification criterion in the learning mode, wherein the machine learning model generates diagnosis information about whether cervical cancer has occurred with respect to the pre-processed photographed cervix image,
- a screen display controller 250 configured to display and output a user interface screen for displaying the diagnosis information and inputting evaluation information according to a reading specialist,
- a retraining data generator 230 configured to extract information required for retraining from the evaluation information input through the user interface screen and request retraining the machine learning model, and
- a diagnosis and evaluation information storage 240 configured to store the diagnosis information about whether cervical cancer has occurred and the evaluation information input through the user interface screen.

For reference, the multi-level classification criteria, the diagnosis information for the subject, and the evaluation information may be stored in the storage medium 300.

The learning data generator 210 applies upper/lower or left/right mirroring or cropping to the learning data for each classification criterion to generate additional learning data to thereby adjust a numerical balance of the learning data generated for each classification criterion in the learning mode so that a specific form of cervical (cancer) image data is prevented from being excessively learned, or conversely, another specific form (or type) of images is prevented from being excluded in normal learning.

Meanwhile, the learning data generator 210 is characterized in which, when classifying the unclassified photographed image data for the cervix, the unclassified photographed image data for the cervix is classified using a combination of at least two classification criteria among a first level classification criterion having a color as a classification criterion, a second level classification criterion having a size of the cervix in photographed image data as a classification criterion, a third level classification criterion having a combination of a color and a form in cervix image data as a classification criterion, and a fourth level classification criterion having an exposure and a focus as a classification criterion.

In a specific implementation method, the learning data generator 210 firstly classifies the unclassified photographed image data for the cervix according to the first level classification criterion having a color as a classification criterion, secondarily classifies the unclassified photographed image data for the cervix according to the second level classification criterion having a size of the cervix in the firstly-classified unclassified photographed image data as a classification criterion, and thirdly classifies the unclassified photographed image data according to the third level classification criterion having a combination of a color and a form in the secondary-classified unclassified photographed image data as a classification criterion.

In addition, the learning data generator 210 may classify the thirdly-classified unclassified photographed image data for the cervix according to the fourth-level classification criterion having an exposure and a focus as a classification criterion. The fourth level classification criterion may be preferentially applied prior to the first level classification criterion and used as learning data for filtering photographed image data that is not diagnosable (e.g., a case in which a lesion is not identified). For example, in response to underexposure/overexposure, the histogram may be extremely skewed to one side, and thus such a characteristic may be used to classify the corresponding photographed image data, and in response to an out-of-focus image, an edge (a boundary line) may not be detected or the color contrast may appear unclear, and thus such a characteristic may be used to classify the corresponding photographed image data (fourth classification).

In addition, the learning data generator 210 firstly classifies the unclassified photographed image data for the cervix according to the first-stage classification criterion having a color as a classification criterion, and the first level classification criterion includes color values for identifying each of one or more images among an acetic acid reaction image, a Lugol's solution reaction image, a green filter image, and a general image as a classification criterion value.

Further, the learning data generator 210 performs the second classification according to the size of the cervix in the firstly-classified unclassified photographed image data, for example, the size of the cervix in the image, such as 150%, 100%, 80%, and 50%, and the size including a colposcope and other parts as a classification criterion.

Further, the learning data generator 210 thirdly classifies the unclassified photographed image data for the cervix according to the third level classification criterion having a combination of a color and a form in cervix photographed data in the secondarily-classified unclassified photographed image data for the cervix as a classification criterion, in which the third level classification criterion includes a combination of a color value and a shape for identifying one or more among blood, mucus, a loop, a colposcope, a treatment trace, and a surgical instrument in the cervix image data as a classification criterion value to classify foreign substance that affects the cervix.

For example, blood mainly appears in the form of a red substance flowing downward from the center of the cervix, mucus appears in the form of a pale yellow substance flowing downward from the center of the cervix, and a loop is mainly located in the center of the cervix and generally appears as a distinct boomerang-shaped wire. A colposcope and other surgical instruments appear in a color (silver, blue, etc.) different from the cervix in pink so that the use of a combination of a color and a shape of each foreign substance may allow the foreign substances affecting the cervix to be classified as illustrated above.

In the above illustrated first to fourth classification processes, each classification may be performed using CNN which is a deep learning technique. In the first, second, and fourth classifications, the features to be extracted are clear, and thus a configuration having only a few layers may enable high-accuracy classification, and in the third classification, a large number of features need to be extracted, and thus a deep layer configuration may be used to increase the accuracy.

Hereinafter, a method of classifying learning data of the automatic cervical cancer diagnosis system 200 according to an embodiment of the present invention will be described in more detail with reference to FIGS. 3 and 4.

Figure 3:
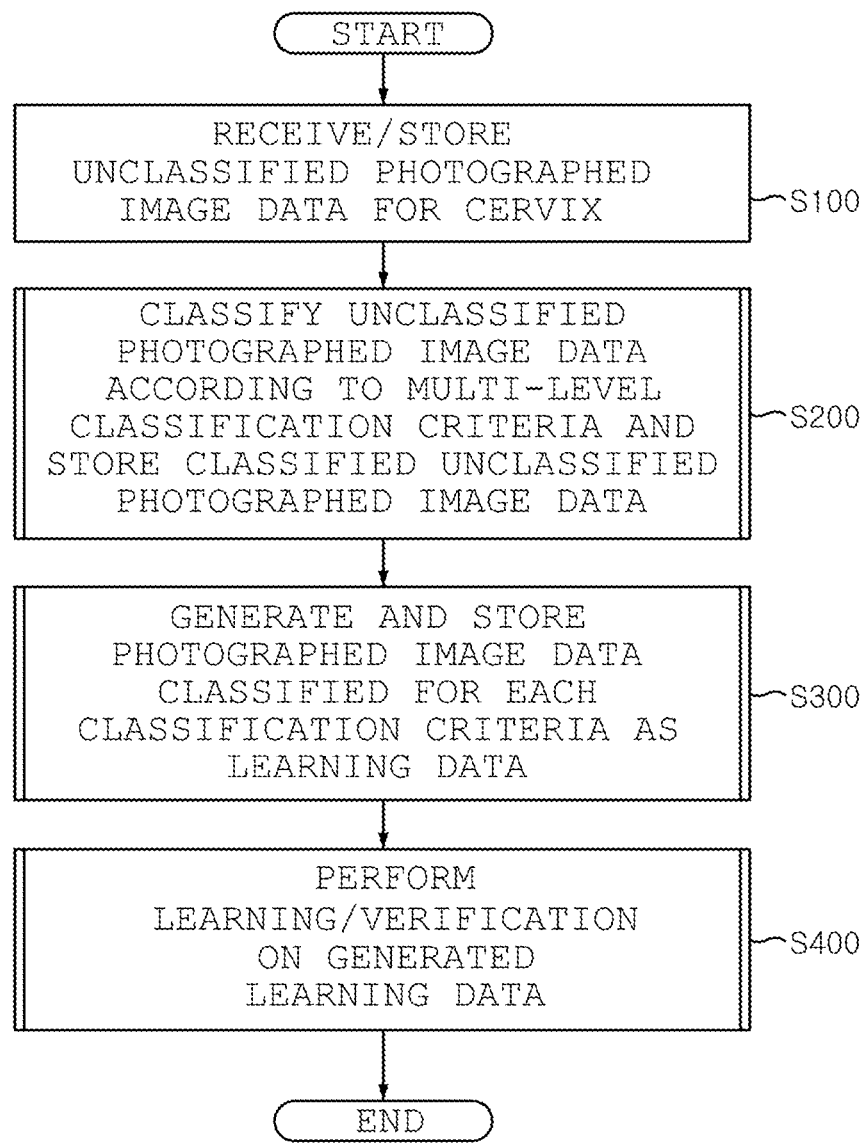
FIG. 3 is a view for describing a method of classifying cervical learning data according to an embodiment of the present invention.
Figure 4:
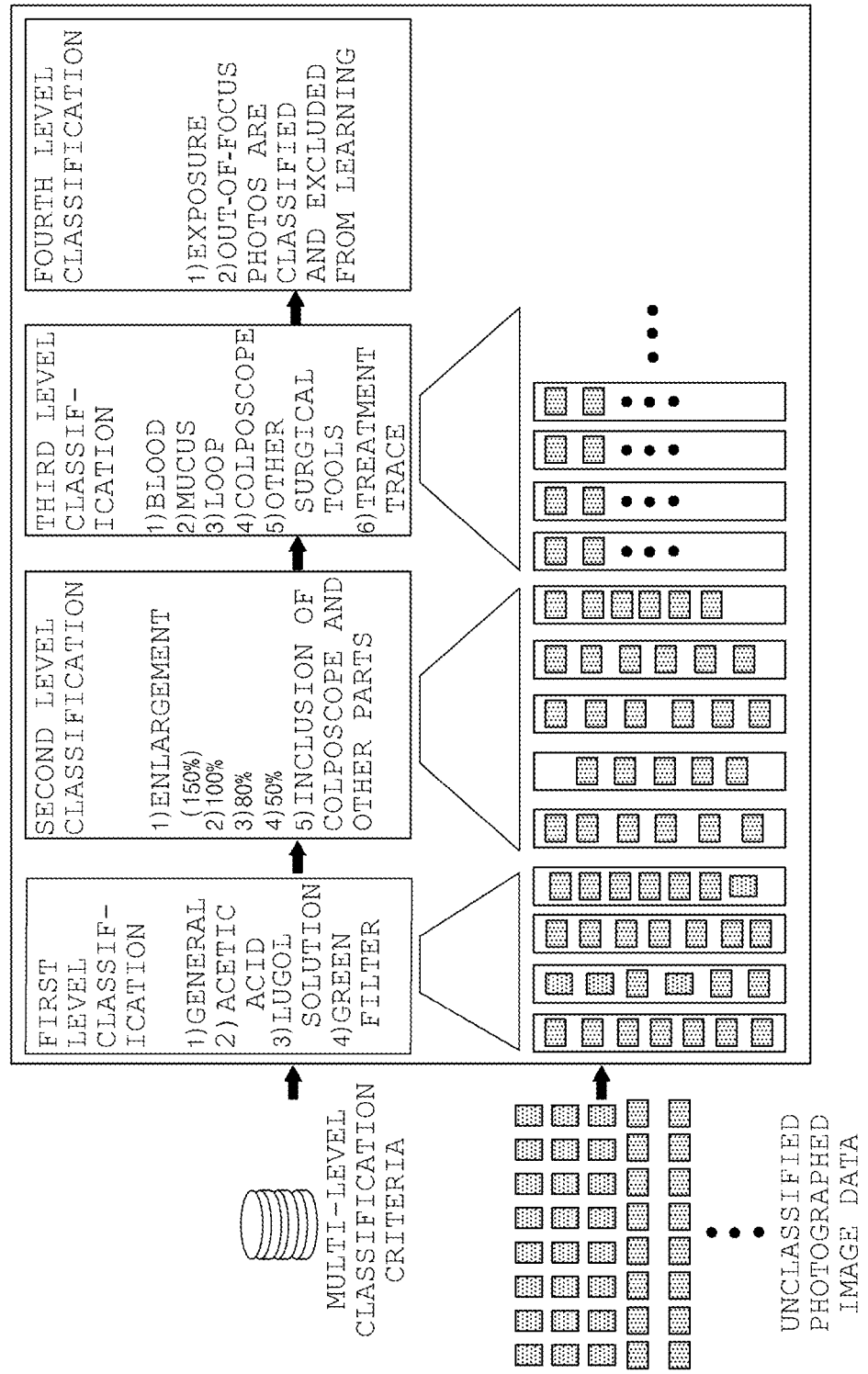
FIG. 4 is a view for specifically describing multi-level classification criteria for generating cervical learning data according to an embodiment of the present invention.

First, FIG. 3 is a view for describing a method of classifying cervical learning data according to an embodiment of the present invention, and FIG. 4 is a view for specifically describing multi-level classification criteria for generating cervical learning data according to an embodiment of the present invention.

Referring to FIG. 3, first, prior to performing learning on unclassified photographed image data for a cervix, it is assumed that pieces of unclassified photographed image data for a cervix transmitted from the imaging device 100 or an external device are being stored in the storage medium 300 (S100) or are stored in the storage medium 300 in advance.

Under the assumption, in response to a command to execute a learning mode received from an administrator, the learning data generator 210 classifies each piece of unclassified photographed image data for the cervix based on a neural network algorithm, such as CNN, in which the pieces of unclassified photographed image data for the cervix are classified according to a combination of a plurality of multi-level classification criteria and stored first (S200)

For example, the learning data generator 210 firstly classifies the unclassified photographed image data for the cervix according to the first level classification criterion having a color as a classification criterion.

For the first classification, the learning data generator 210 may include color values for identifying each of an acetic acid reaction image, a Lugol's solution reaction image, a green filter image, and a general image as a classification criterion value, to classify the above four images.

Specifically, the acetic acid reaction image may show a white stain on the cervix so that the white stain is distinguished from the cervix and vagina in a pink color. The Lugol's solution reaction image shows a brown or dark orange color, and the green filter image shows a strong green color over the entire area of the image so that the use of the color value representing the characteristic of each image as a classification criterion value may allow unclassified photographed image data for the cervix to be classified.

When the first classification is completed, the learning data generator 210 performs the second classification according to the second level classification criterion having a size of the cervix in the first classified photographed image data.

The cervix is a circular shape having a size corresponding to a 500-Won coin and is generally located in the center of the image. Therefore, based on the size of the cervix (150%, 100%, 80%, etc.) in the image, the photographed data is secondarily classified, for example, into an image showing only the cervix enlarged, an image showing the entire cervix, an image showing the cervix in a region of 80% of the image, an image showing the cervix in a region of 50% of the image, and an image including the cervix, the colposcope, and other parts may be secondarily classified.

Thereafter, the learning data generator 210 thirdly classifies foreign substances affecting the cervix according to the third level classification criterion that has a combination of a color and a shape in the secondly-classified cervix image data.

As described above, blood mainly appears in the form of a red substance flowing downward from the center of the cervix, mucus appears in the form of a pale yellow substance flowing downward from the center of the cervix, and a loop is mainly located in the center of the cervix and generally appears as a distinct boomerang-shaped wire. A colposcope and other surgical instruments appear in a color (silver, blue, etc.) different from a pink color of the cervix so that the use of a combination of a color and a shape of each foreign substance may allow the foreign substances affecting the cervix to be classified as illustrated above.

The photographed image data for each classification criterion classified according to a combination of the multi-level classification criteria as described above may be temporarily stored in the storage medium 300 or the memory in the system 200.

When the classification of the unclassified photographed image data is completed, the learning data generator 210 generates the photographed image data for the cervix classified for each classification criteria as learning data for each classification criteria and stores the generated learning data for each classification criteria in the storage medium 300 (S300). In the process of generating the learning data, the learning data generator 210 may further generate additional learning data to adjust the numerical balance of the learning data for each classification criterion, and the additional learning data may be generated based on the learning data for each classification criterion.

As a method of generating the additional learning data, mirroring may be used as vertical mirroring in which left and right sides are inverted and horizontal mirroring in which upper and lower sides are inverted, or cropping may be used such that cropping is executed at a size smaller than the original size based on top/bottom/left/right to generate additional learning data. In addition, when mirroring and cropping are used together, up to 16 times more additional learning data may be generated.

For reference, in the above example, the learning data is generated by employing a combination of the first, second, and third level classification criteria, but the learning data may be generated by employing a combination of the first and second level classification criteria, a combination of the first and third level classification criteria, and a combination of the second and third level classification criteria, and as shown in FIG. 4, unclassified photographed image data for the cervix may be classified by individually employing the first to third level classification criteria, and the classified image data may be used as learning data for each classification criterion.

As described above, when the unclassified photographed image data for the cervix is classified according to a combination of the multi-level classification criteria and the learning data is generated, the machine learning model 262 for the cervix performs learning and verification on the features of the learning data generated for each classification criterion (S400). When unclassified photographed image data for the cervix is additionally obtained, the above-described learning mode is performed again.

As described above, since the automatic cervical cancer diagnosis system 200 according to the embodiment of the present invention generates learning data by classifying unclassified photographed image data for the cervix according to a combination of multi-level classification criteria, the number of classifications of learning data increases and as the number of classifications of the learning data increases, image data having various characteristics is learned so that the presence or absence of a lesion may be more accurately diagnosed.

In addition, the present invention further generates additional learning data to adjust the numerical balance of learning data for each classification criterion and uses the additional learning data for learning so that excessive learning is prevented from being performed on a specific form (type) of cervical (cancer) image data, or conversely, no learning is prevented from being performed on another specific form of cervical image data, thereby providing the effect of accurately diagnosing the presence or absence of lesions on the cervix.

Hereinafter, a process of automatically diagnosing cervical cancer using the automatic cervical cancer diagnosis system 200 that trains the machine learning model 262 using the learning data generated by classifying the unclassified image data for the cervix according to the combination of the above-described multi-level classification criteria will be described.

Figure 5:
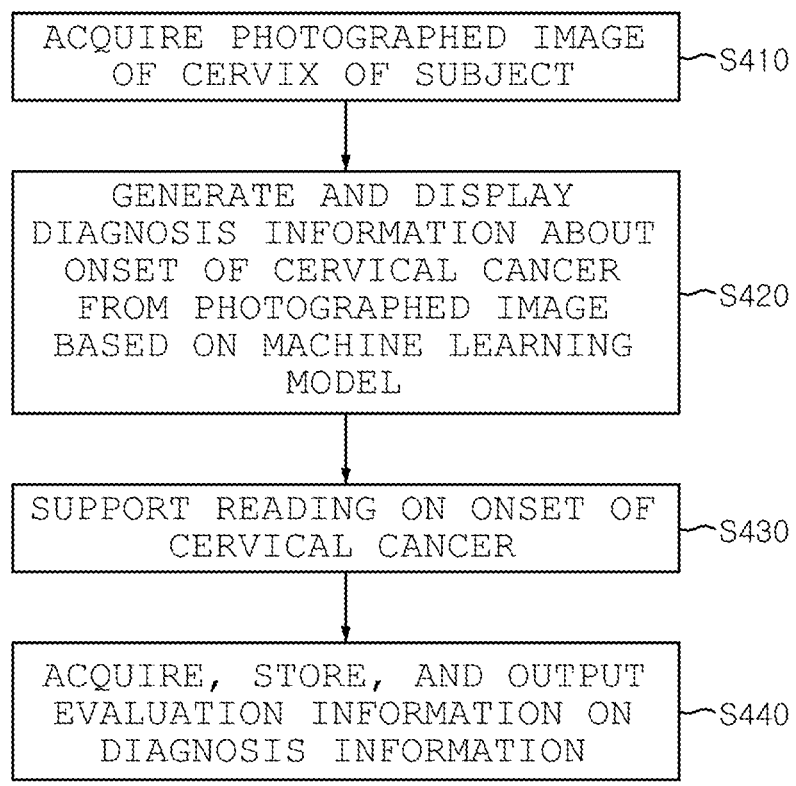
FIG. 5 is a view for describing a process of automatically diagnosing cervical cancer according to an embodiment of the present invention.

FIG. 5 is a view for describing a process of automatically diagnosing cervical cancer according to an embodiment of the present invention. FIGS. 6A to 6E are exemplary views illustrating a user interface (UI) screen provided in a process of automatically diagnosing cervical cancer according to an embodiment of the present invention.

Figure 6A:
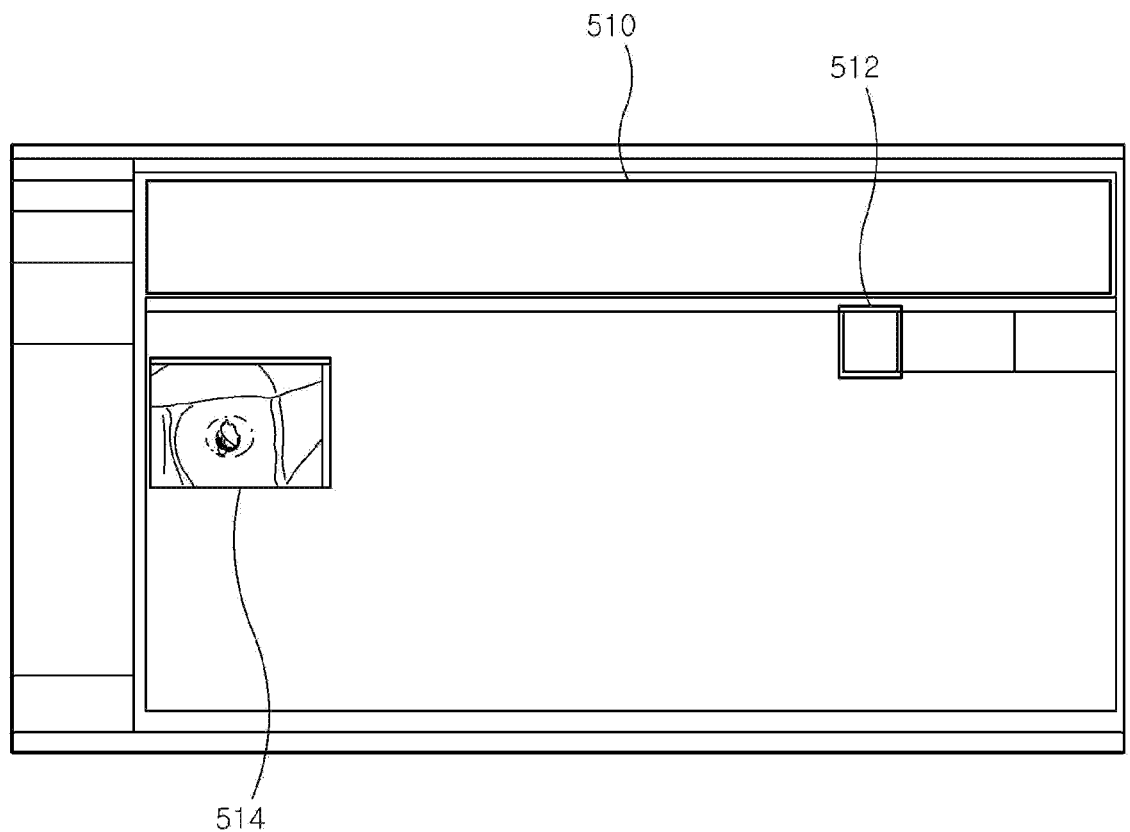
FIGS. 6A to 6E are exemplary views illustrating a user interface (UI) screen provided in a process of automatically diagnosing cervical cancer according to an embodiment of the present invention.

Referring to FIG. 5, first, in a diagnosis mode, the automatic cervical cancer diagnosis system 200 acquires a photographed image of the cervix of the subject (S410). The photographed image of the cervix of the subject may be acquired from the imaging device 100 or may be acquired from the outside through the communicator 400 or a storage medium. The photographed image 514 of the cervix acquired as described above is displayed on a UI screen as shown in FIG. 6A by the screen display controller 250. The UI screen may be configured such that information about a subject, which is a patient, is displayed through a subject information input area 510 together with the photographed image 514 as shown in FIG. 6A.

In order to generate more accurate diagnosis information prior to displaying the acquired photographed image of the cervix of the subject on the UI screen, the image pre-processor 220 may preferably perform pre-processing on the photographed image of the cervix. Here, the pre-processing may include at least one of red-green-blue (RGB)-hue-saturation-value (HSV) conversion for robustness against illumination and noise of the photographed image, image quality improvement through histogram smoothing, etc., blurring, and noise processing. Referring again to FIG. 5, when the photographed image of the cervix of the subject is acquired and is completed with pre-processing, the machine learning model 262 of the cervical cancer diagnoser 260 generates diagnosis information about whether cervical cancer has occurred with respect to the pre-processed photographed cervix image (S420).

The machine learning model 262 generates the diagnosis information about whether cervical cancer has occurred using a plurality of pieces of previously-input training information, that is, information including (i) learning data for each classification criterion according to a combination of multi-level classification criteria, (ii) data indicating whether a lesion of cervical cancer is present in a plurality of images of the learning data, and in response to presence of the lesion, (iii) data showing a part of the image in which the lesion is present. For reference, the machine learning model 262 may be a CNN model, or a model combining a CNN and a support vector machine (SVM).

In order to increase the accuracy and reliability of the machine learning model 262, a large amount of learning data for training is required, and the more learning data for training, the more accurate and reliable the machine learning model may be.

On the other hand, the diagnosis information may include classification information regarding a status of being negative, atypical, positive, or malignant for cervical cancer. In addition, the classification information may include probability information indicating how accurate the classification is.

Figure 6B:
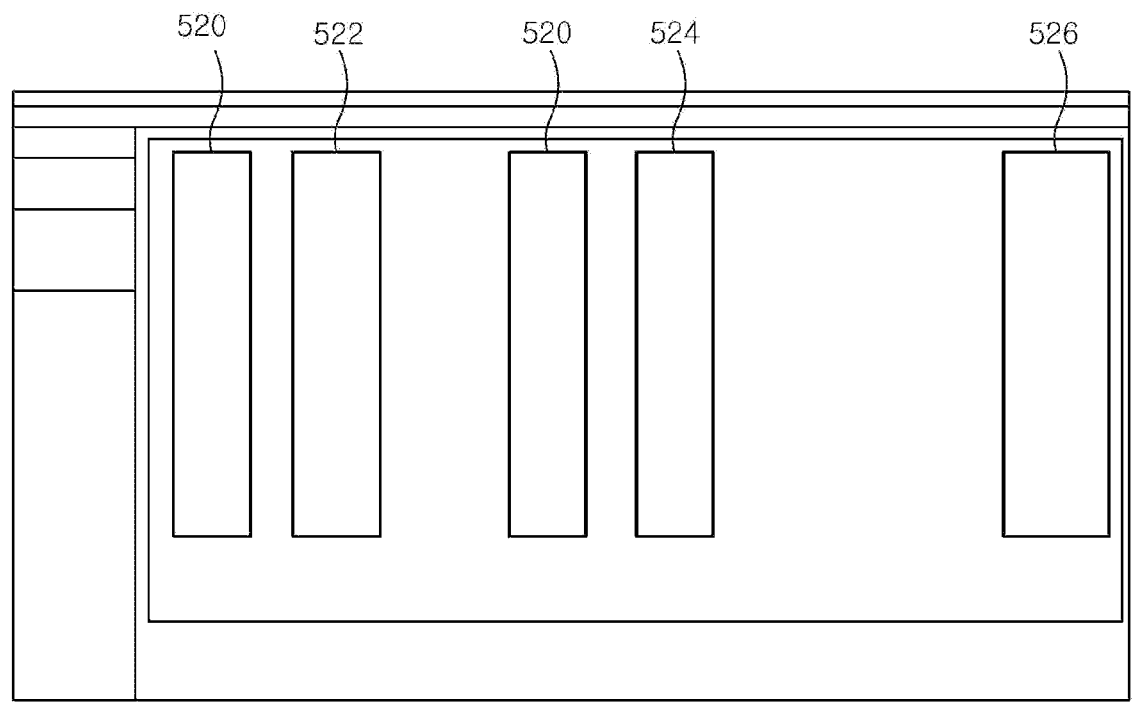

In more detail, the diagnosis information may include negative/positive information, that is, information indicating whether a cervical cancer diagnosis is negative or not and in response to cervical cancer being positive, indicating a low cancer risk or high cancer risk and may further include morphological opinion information, such as acetowhite epithelium, mosaic, erosion or ulceration, irregular surface contour, punctation, atypical vessels, discoloration, etc. The diagnosis information may be listed and provided to correspond to a plurality of the photographed images 514 by the screen display controller 250 as shown in FIG. 6B. The UI screen shown in FIG. 6B displays subject information 520, input time point information 522, and information indicating whether the onset of cervical cancer is suspected according to classification information and probability information calculated by the machine learning model 262 (marked 'suspicious'; 524). Further, the UI screen shown in FIG. 6B displays "Evaluation" buttons 526 corresponding to a specific photographed image such that operations subsequent to operation S420 continue.

Through the "Evaluation" button 526, a reading specialist may read a diagnosis regarding whether cervical cancer has occurred that is automatically diagnosed based on the machine learning model and may input evaluation information. That is, in response to manipulation of the "Evaluation" button 526, the screen display controller 250 supports multiple screens for reading whether cervical cancer has occurred.

Figure 6C:
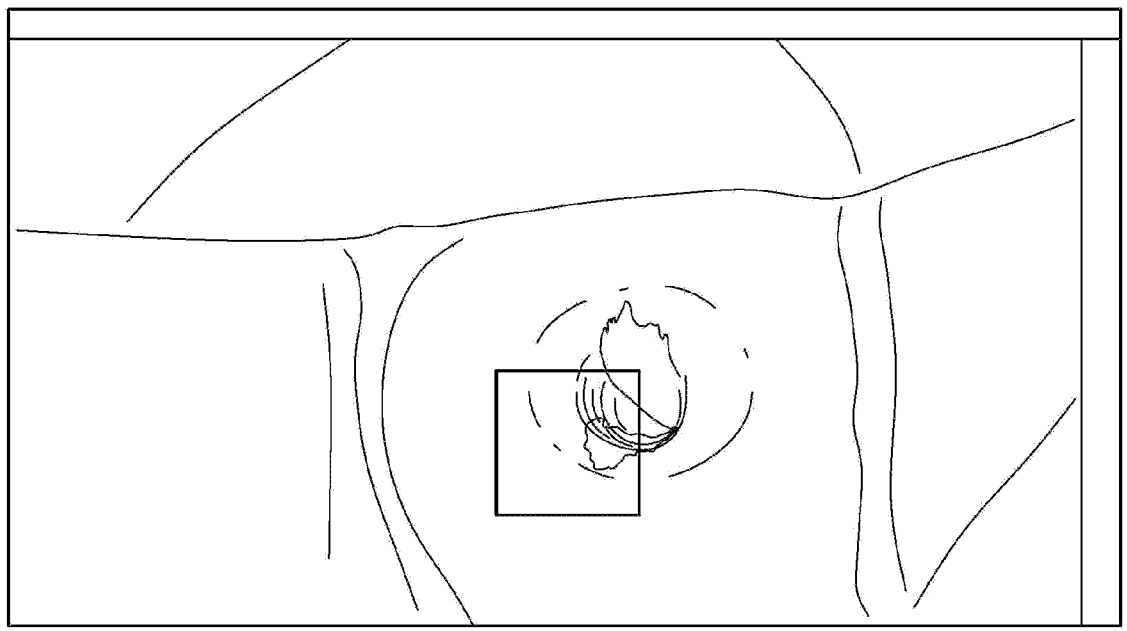

For example, as shown in FIG. 6C, all or part of the photographed images are provided on the UI screen so that the reading specialist may mark various required indications (e.g., a rectangle, an arrow, a text input, etc.) while determining whether a medically unusual area is present.

In addition, the screen display controller 250 may display diagnosis information corresponding to a reading specialist command input through the UI screen and support input of evaluation information by the reading specialist (S430).

The evaluation information may include information indicating whether the provided diagnosis information is accurate, that is, information on whether the onset included in the diagnosis information is correct or incorrect, information on whether the classification information included in the diagnosis information is correct or incorrect, and information indicating what classification is correct when the classification information is incorrect.

In addition, the evaluation information may include information on the quality of the photographed image, for example, information on technical defects of the photographed image. For example, the technical defects may include a difficulty in accurately performing determination on the photographed image due to excessive mucus or blood in the photographed image, a difficulty in determining whether cervical cancer has occurred due to the angle of the photographed image or the location of the photographed part, an insufficient acetic acid reaction when an acetic acid reaction is needed, or image defects, such as being out of focus, overexposure, or underexposure.

Figure 6D:
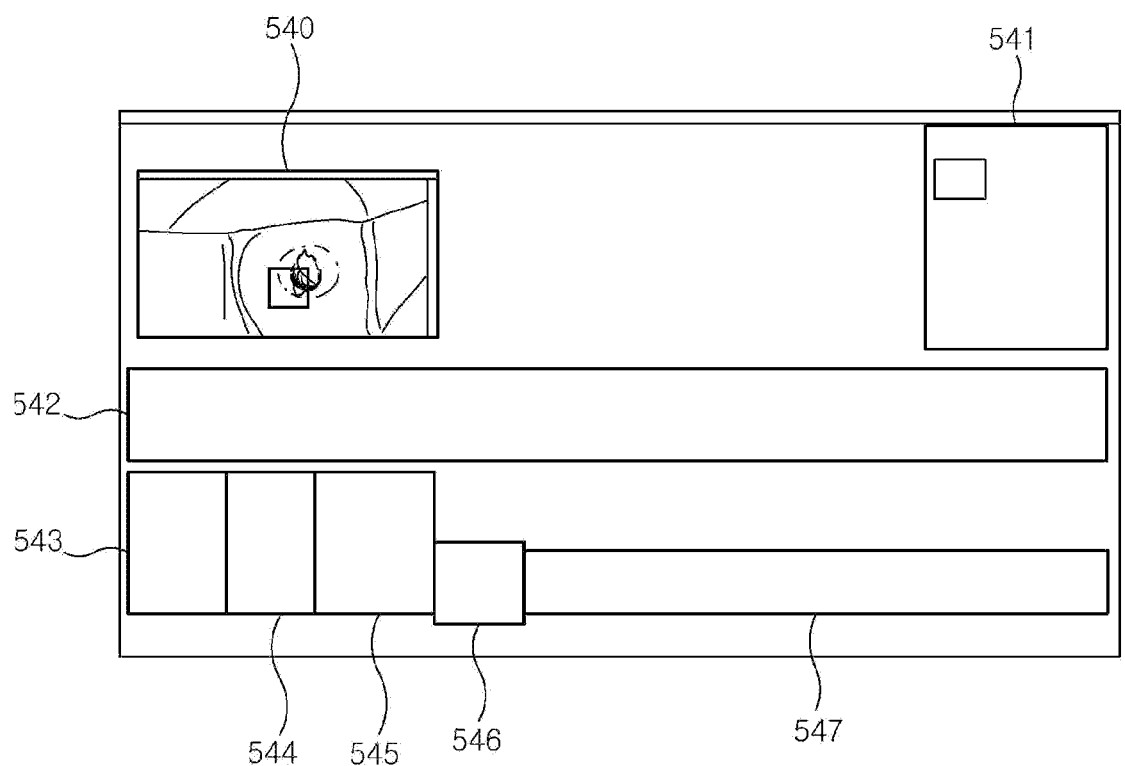

FIG. 6D shows a UI screen displayed by the screen display controller 250, in which an area for displaying the entire area or a part of the photographed image 540, an area for displaying history information 541 of another image of the same subject photographed at a previous time, a subject information exposure area 542 illustrated in FIG. 6A, a negative/positive determination information area 543 for inputting negative/positive determination information, a morphological opinion information input area 544 for inputting morphological opinion information by a reading specialist, a technical defect information input area 545 for inputting information regarding the quality of the photographed image 540, an artificial intelligence diagnosis information output area 546 for displaying diagnosis information derived based on the machine learning model 262, and a user opinion input area 547 for inputting an opinion based on the photographed image by the reading specialist are shown so that the reading specialist may easily evaluate the onset of cervical cancer corresponding to the automatic diagnosis information.

On the other hand, when the reading specialist inputs evaluation information regarding the diagnosis information analyzed based on the photographed image of the cervix of the subject and the machine learning model 262 through the UI screen shown in FIG. 6, the diagnosis and evaluation information storage 240 stores the diagnosis information regarding whether cervical cancer has occurred and the evaluation information input by the reading specialist through the UI screen in the storage medium 300 (S440), or outputs the diagnosis information and the evaluation information to the display 500 upon request of an administrator or a reading specialist.

On the other hand, when the evaluation information is input through the UI screen, the retraining data generator 230 may extract information required for retraining from the evaluation information input through the UI screen, for example, negative/positive determination information, technical defect information, and the like, and request retraining the machine learning model 262.

Figure 6E:
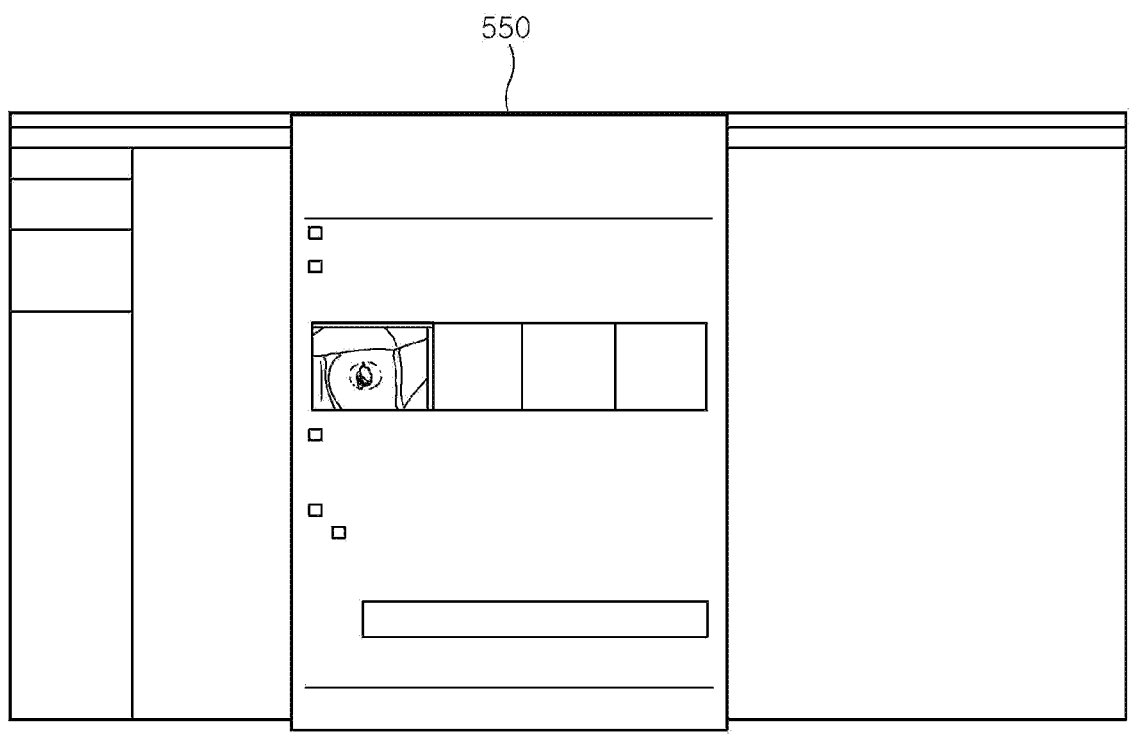

In addition, the above-described evaluation information may be processed and provided in the form of a medical result report. For example, the UI provided for the medical result report is shown in FIG. 6E, and a medical result report 550 may include information about the onset of cervical cancer, classification information, and the like. The medical result report may be provided through another device located far from a place where the photographed image is initially acquired (i.e., a photography place) or a place where the photographed image is read. The above embodiments have been described on the assumption that the reading specialist is located at the automatic cervical cancer diagnosis system 200 and inputs the evaluation information, but alternatively, pieces of diagnosis information may be transmitted to the reading specialist located at a remote site through the communicator 400 so that the reading specialist may input evaluation information.

According to the embodiment of the present invention described above, since the onset of cervical cancer may be automatically diagnosed based on the machine learning model 262 pre-learned in advance, the onset of cervical cancer may be more quickly and accurately diagnosed compared to the conventional method in which the medical staff directly checks the condition of the cervix based on education and experience by directly viewing acquired photographed cervix images through a colposcope.

In addition, the present invention may perform more accurate reading by reusing evaluation information as data for retraining the machine learning model.

Figure 7:
FIG. 7 shows exemplary views illustrating malignant atypical vessels.

Meanwhile, in the above-described embodiment, the first level classification criterion having a color as a classification criterion, the second level classification criterion having the size of the cervix in the photographed image data as a classification criterion, the third level classification criterion having a combination of a color and a shape in the cervix image data as a classification criterion, and the fourth level classification criterion having an exposure and a focus as a classification criterion are illustrated, but the learning data generator 210 may further include a fifth level classification criterion having a malignant atypical vascular pattern as a classification criterion as shown in FIG. 7 and may generate learning data by classifying the unclassified photographed image data for the cervix according to the fifth level classification criterion alone or a combination of the fifth level classification criterion and other classification criteria described above.

After learning of a malignant atypical vascular pattern shown in FIG. 7 is performed, the cervical cancer diagnoser 260 may generate a diagnosis regarding the onset of cervical cancer indicating a malignant atypical vascular pattern based on the trained machine learning model.

On the basis of the above exemplary embodiment, it should be understood by one of ordinary skill in the art that the present invention can be achieved by a combination of software and hardware or only by hardware. Meanwhile, objects of the technical solution of the present invention or portions contributing to the prior art may be implemented in the form of program instructions executable by various computer components and may be recorded in a computer-readable recording medium. The computer-readable recording medium may include program instructions, data files, data structures, and the like alone or in combination thereof. The program instructions recorded in the computer-readable medium may be program instructions specially designed and constructed for the present invention or may be program instructions known to those skilled in the art of computer software.

Examples of the computer-recordable medium include magnetic media, such as hard disks, floppy disks, and magnetic tape; optical media such as a compact disc-read only memory (CD-ROM), a digital versatile disc (DVD); magneto-optical media, such as floptical disks; and hardware devices specially constructed to store and execute program instructions such as a ROM, a random access memory (RAM). Examples of the program instructions include both machine code, such as that produced by a compiler, and higher level codes that may be executed by the computer using an interpreter. The above-described hardware devices may be configured to act as one or more software modules in order to perform the operations of the above-described embodiments, or one or more software modules may be configured to act as the above-described hardware devices, or vice versa. In addition, the hardware device may include a processor, such as a central processing unit (CPU) or graphic processor unit (GPU), which is connected to a memory such as a ROM/a RAM for storing program instructions and configured to execute the instructions stored in the memory and may include a communicator configured to transmit or receive a signal to or from an external device. In addition, the hardware device may include a keyboard, a mouse, and other external input devices for receiving instructions written by developers.

The above description of the invention is for illustrative purposes, and a person having ordinary skills in the art should appreciate that other specific modifications may be easily made without departing from the technical spirit or essential features of the invention. Therefore, the exemplary embodiments disclosed in the present invention and the accompanying drawings are intended to illustrate and not limit the technical spirit of the present invention, and the scope of the present invention is not defined by the detailed description set forth above but by the accompanying claims of the invention.

What is claimed is:

1. An automatic cervical cancer diagnosis system comprising:
a learning data generator configured to classify unclassified photographed image data for a cervix transmitted from an external device or a storage according to one or a combination of multi-level classification criteria to generate learning data for each new classification criterion in a learning mode;
a photographed image pre-processor configured to pre-process photographed cervix images;
a cervical cancer diagnoser including a machine learning model for cervical cancer that learns a characteristic of the learning data generated for each classification criterion in the learning mode, wherein the machine learning model generates diagnosis information about whether cervical cancer has occurred with respect to the pre-processed photographed cervix image;
a screen display controller configured to display and output a user interface screen configured to display the diagnosis information and inputting evaluation information according to a reading specialist;
a retraining data generator configured to extract information required for retraining from the evaluation information input through the user interface screen and request retraining the machine learning model; and
a diagnosis and evaluation information storage configured to store the diagnosis information about whether cervical cancer has occurred and the evaluation information input through the user interface screen.

2. The automatic cervical cancer diagnosis system of claim 1, wherein the learning data generator applies mirroring or cropping to the learning data for each classification criterion to generate additional learning data such that a numerical balance of the learning data for each classification criterion is adjusted.

3. The automatic cervical cancer diagnosis system of claim 1, wherein the learning data generator classifies the unclassified photographed image data using a combination of at least two classification criteria among a first level classification criterion having a color as a classification criterion, a second level classification criterion having a size of the cervix in photographed image data as a classification criterion, a third level classification criterion having a combination of a color and a form in cervical image data as a classification criterion, and a fourth level classification criterion having an exposure and a focus as a classification criterion.

4. The automatic cervical cancer diagnosis system of claim 1, wherein the learning data generator firstly classifies the unclassified photographed image data for the cervix according to a first level classification criterion having a color as a classification criterion, secondarily classifies the unclassified photographed image data for the cervix according to a second level classification criterion having a size of the cervix in the firstly-classified unclassified photographed image data as a classification criterion, and thirdly classifies the unclassified photographed image data according to a third level classification criterion having a combination of a color and a form in the secondarily-classified unclassified photographed image data as a classification criterion.

5. The automatic cervical cancer diagnosis system of claim 3, wherein the first level classification criterion includes color values for identifying each of an acetic acid reaction image, a Lugol's solution reaction image, a green filter image, and a general image as a classification criterion value, and
the third level classification criterion includes a combination of a color value and a shape for identifying one or more among blood, mucus, a loop, a colposcope, a treatment trace, and a surgical instrument in the cervical image data as a classification criterion value.

6. The automatic cervical cancer diagnosis system of claim 1, wherein the cervical cancer diagnoser generates the diagnosis information including classification information regarding being negative, atypical, benign, and malignant for cervical cancer with respect to a photographed cervix image of a subject, accuracy information of the classification information, negative/positive determination information, and morphological opinion information based on the machine learning model.

7. The automatic cervical cancer diagnosis system of claim 1, wherein the screen display controller displays and outputs a screen that is divided into an entire or partial display area of a photographed cervix image of a subject, a history information display area of another image of the subject photographed at a previous time, a subject information exposure area, a negative/positive determination information input area, a morphological opinion information input area, a technical defect information input area regarding a quality of a photographed image, an output area of the diagnosis information derived based on the machine learning model, and a reading specialist opinion input area as the user interface screen.

8. The automatic cervical cancer diagnosis system of claim 1, wherein the multi-level classification criteria include a malignant atypical vascular pattern as a classification criterion.

9. The automatic cervical cancer diagnosis system of claim 1, wherein the learning data generator classifies the unclassified photographed image data using each or a combination of at least two classification criteria of a first level classification criterion having a color as a classification criterion, a second level classification criterion having a size of the cervix in photographed image data as a classification criterion, a third level classification criterion having a combination of a color and a form in cervical image data as a classification criterion, a fourth level classification criterion having an exposure and a focus as a classification criterion, and a fifth level classification criterion having a malignant atypical vascular pattern as a classification criterion.

10. The automatic cervical cancer diagnosis system of claim 4, wherein the first level classification criterion includes color values for identifying each of an acetic acid reaction image, a Lugol's solution reaction image, a green filter image, and a general image as a classification criterion value, and
the third level classification criterion includes a combination of a color value and a shape for identifying one or more among blood, mucus, a loop, a colposcope, a treatment trace, and a surgical instrument in the cervical image data as a classification criterion value.

* * * * *